United States Patent
Poizat et al.

(10) Patent No.: US 6,705,168 B2
(45) Date of Patent: Mar. 16, 2004

(54) PROCESS AND DEVICE FOR PROCESSING OF VIBRATION MEASUREMENTS OF A ROTATING MACHINE ROTOR

(75) Inventors: Philippe Poizat, Marcilly d'Azergues (FR); Patrick Labeyrie, Ventabren (FR)

(73) Assignee: Ol db Acoustics & Vibration, Limonest Cedex (FR)

(*) Notice: Subject to any disclaimer, the term of this patent is extended or adjusted under 35 U.S.C. 154(b) by 0 days.

(21) Appl. No.: 10/364,677

(22) Filed: Feb. 12, 2003

(65) Prior Publication Data

US 2003/0172738 A1 Sep. 18, 2003

(30) Foreign Application Priority Data

Feb. 12, 2002 (FR) .............................. 02 01677

(51) Int. Cl.$^7$ .............................. G01H 13/00
(52) U.S. Cl. ..................................... 73/579; 73/593
(58) Field of Search ............... 73/660, 659, 658, 73/649, 570, 579, 593, 602

(56) References Cited

U.S. PATENT DOCUMENTS

| | | |
|---|---|---|
| 4,464,935 A | 8/1984 | McHugh |
| 4,607,529 A | 8/1986 | Morey |
| 5,533,400 A | 7/1996 | Gasch et al. |
| 5,588,805 A | 12/1996 | Geringer |
| 6,026,348 A | 2/2000 | Hala |

Primary Examiner—Richard A. Moller
(74) Attorney, Agent, or Firm—Dennison, Schultz, Dougherty & MacDonald

(57) ABSTRACT

The processing method, starting from the measurements of the vibration of a bearing block (5) or a rotor (2) of a rotating machine (3) consists particularly of:

starting from spectral decompositions [$Ax(f_i)$, $\Phi x(f_i)$] and [$Ay(f_i)$, $\Phi y(f_i)$], calculating a spectral decomposition in elementary elliptical trajectories of the displacement of the rotor axis, defined by a series of sets of at least three data [$Emax(f_i)$, $Emin(f_i)$, $E\phi(f_i)$] where:

$Emax(f_i)$ is the maximum radius of the elementary ellipse at frequency $f_i$, $Emin(f_i)$ is the minimum radius of the elementary ellipse at frequency $f_i$, $E\phi(f_i)$ corresponds to the value of the orientation angle of the principal axis of the elementary ellipse, and may be positive or negative depending on the direction of movement around the ellipse.

Save the series [$Emax(f_i)$, $Emin(f_i)$, $E\phi(f_i)$].

12 Claims, 3 Drawing Sheets

PROCESS AND DEVICE FOR PROCESSING OF VIBRATION MEASUREMENTS OF A ROTATING MACHINE ROTOR

This invention relates to the technical domain of measuring, recording and studying the vibrations of a bearing block or the rotor of a rotating machine.

In this domain, it is known how to use at least two position sensors placed relative to the bearing block so as to measure the shaft displacements, for example to study the rotational behavior of a shaft guided by an oil bearing block. The two position sensors are then arranged in the same plane, approximately perpendicular to the direction of rotation, along two approximately orthogonal measurement directions X and Y. The sensors are used to make a series of measurements x(t) and y(t) that can be considered as being the instantaneous coordinates of the axis of the shaft supported by the bearing block. Two seismic sensors, for example accelerometers, can also be used for the study of the vibrations of the bearing block. It is also known how to use means of measuring the rotation speed ω(t) of the shaft, in order to complete this information.

After acquisition, the measured magnitudes are recorded on an appropriate support or data storage device. Considering the large number of measurements made, it then may be necessary to compress data to reduce the volume.

In general, this compression is done by calculating a DFT (Discrete Fourier Transform) for each of the two series x(t) and y(t) to obtain a spectral decomposition of the x(t) and y(t) series in amplitude and phase according to an amplitude-phase couple [Ax($f_i$), Φx($f_i$)] and [Ay($f_i$), Φy($f_i$)], in which $f_i$ corresponds to frequency values distributed on the frequency spectrum and is usually chosen so as to correspond to integer multiples or an integer fraction of the rotation speed.

This type of processing by a Fourier Transform can significantly reduce the data volume to be stored to the extent that it is possible to record the spectral amplitude-phase decomposition that includes a limited number of terms, instead of the measurements themselves.

However in practice, in cases in which prolonged test campaigns are carried out involving a large number of measurements, it was found that the individual spectral decomposition of each measurement series x(t), y(t) represents a relatively large data volume and for which the compression factor is not sufficient.

Furthermore, individual spectral decomposition data for x(t) and y(t) measurements cannot be used directly to make a detailed analysis of the behavior of the bearing block or the rotating element being studied.

Therefore, it appears necessary to have a new processing technique capable firstly of reducing the volume of data to be stored without introducing any bias or excessive distortion, while providing data that can be used directly and in particular that are useful for an intuitive analysis of the behavior of the rotating element being studied.

In order to achieve these objectives, the invention relates to a process for processing measurements of the vibration of a rotor of a rotating machine, of the type consisting particularly of:

using a record of at least one pair of two series of measurements x(t) and y(t) made using at least one pair of two position sensors placed relative to the rotor and arranged approximately in the same plane and with two approximately orthogonal measurement directions X and Y, calculate a DFT (Discrete Fourier Transform) of each of the two series x(t) and y(t) to obtain a spectral decomposition of the series x(t) and y(t) in amplitude and phase according to two series of amplitude-phase pairs [Ax($f_i$), Φx($f_i$)] and [Ay($f_i$), Φy($f_i$)], where $f_i$ corresponds to frequency values distributed on the frequency spectrum, According to the invention, this process also consists of:

starting from spectral decompositions [Ax($f_i$), Φx($f_i$)] and [Ay($f_i$), Φy($f_i$)], calculating a spectral decomposition in elementary elliptical trajectories of the displacement of the rotor axis, defined by a series of sets of at least three data [Emax($f_i$), Emin($f_i$), Eφ($f_i$)] where:

Emax($f_i$) is the maximum radius of the elementary ellipse at frequency $f_i$,

Emin($f_i$) is the minimum radius of the elementary ellipse at frequency $f_i$,

Eφ($f_i$) corresponds to the value of the orientation angle of the principal axis of the elementary ellipse (between 0 and 180°), and may be positive or negative depending on the direction of movement around the ellipse, save the series [Emax($f_i$), Emin ($f_i$), Eφ($f_i$)].

It appears that this new processing process has the advantage that it reduces the volume of data to be stored by about a quarter, because three parameters Emax(fi), Emin(fi), Eφ($f_i$) replace the four parameters [Ax($f_i$), Φx($f_i$)] and [Ay ($f_i$), Φy($f_i$)] in the spectral decomposition.

Furthermore, the three data [Emax($f_i$), Emin($f_i$), Eφ($f_i$)] supply characteristic magnitudes of the elementary ellipse corresponding to the trajectory for frequency $f_i$ in the X, Y plane of the axis of the rotating element being studied, for each frequency $f_i$ in the spectral decomposition.

Thus, knowledge of these three parameters is a means of almost immediately perceiving the behavior of the rotating element being studied at frequency $f_i$.

According to the invention, the [Emax($f_i$), Emin($f_i$), Eφ($f_i$)] coefficients may be calculated in different ways starting from spectral decompositions [Ax($f_i$), Φx($f_i$)] and [Ay($f_i$), Φy($f_i$)].

Thus, according to a first variant embodiment, the processing in the method according to the invention is as follows:

use a FFT (Fast Fourier Transform) algorithm using complex numbers, and applied to the signal x(t)+jy(t), make a spectral decomposition of the rotation movement, firstly for positive frequencies and secondly for negative frequencies, giving two series [A($f_i$), Φ($f_i$)] and [A($-f_i$), Φ($-f_i$)], starting from positive frequency spectra and negative frequency spectra, calculate the spectral decomposition into elementary ellipses using the following formulas:

$$Emax(f_i)=[A(f_i)+A(f_i)]/2$$

$$Emin(f_i)=Abs[(A(f_i)-A(-f_i)]/2]$$

$$S(f_i)=Sign[A(f_i)-A(-f_i)]$$

$$E\phi_o(f_i)=[\Phi(f_i)+\Phi(-f_i)]/2$$

$$E\phi(f_i)=S(f_i)\times E\phi_o(f_i)$$

According to a second variant embodiment of the method, the processing is done particularly as follows:

make a DFT-sin (Discrete Fourier Transform in sine) of the x(t) and y(t) series to obtain a spectral decomposition [Ax($f_i$), Φx($f_i$)] and [Ay($f_i$), Φy($f_i$)] in sine, use the sine spectral compositions to make a spectral decomposition into elementary ellipses [Emax($f_i$), Emin($f_i$), Eφ($f_i$)].

According to another characteristic of the invention, the measurements x(t) and y(t), are made jointly with a measurement of the rotation speed ω of the rotor being studied to determine the behavior of the rotor as a function of its rotation speed ω.

And, according to another characteristic of the invention, the processing method consists particularly of the following steps:

make a record of several pairs of series of measurements x(t) and y(t), each pair [x(t), y(t)] being associated with a rotation speed ω(t) of the rotor associating the corresponding rotation speed ω with the spectral decomposition of each pair x(t), y(t), into amplitude-phase [Ax($f_i$), Φx($f_i$)] and [Ay($f_i$), Φx($f_i$)]

associating the rotation speed ω with the spectral decomposition into elementary elliptical trajectories [Emax($f_i$), Emin($f_i$), Eφ($f_i$)]

record the set [ω[Emax($f_i$), Emin($f_i$), Eφ($f_i$)]].

The results of the calculation steps, and particularly the spectral decomposition into elementary ellipses of the studied rotor movement, can then be used in different ways depending on the choices of a user of the method or depending on the type of rotating machine being studied.

Thus, according to one characteristic of the invention, the method includes the following steps:

select a rotation speed $ω_0$, extract the spectral decomposition into elementary ellipses [Emax($f_i$), Emin($f_i$), Eφ($f_i$)] associated with $ω_0$, from the record, and represent the spectral decomposition into elementary ellipses [Emax($f_i$), Emin($f_i$), Eφ($f_i$)], for this value of the rotation speed, using three graphs in an orthogonal coordinate system in which the abscissas axis corresponds to the frequencies.

According to another characteristic of the invention, the processing method may also include the following steps:

select a given frequency $f_0$ in the decomposition spectrum, where $f_0$ is a multiple $Aω_0$ of the rotation speed $ω_0$ for this frequency $f_0$ and for each rotation speed, extract the values Emax($f_0$), Emin($f_0$), Eφ($f_0$), and make a graphic <<Bode>> representation of the coefficients Emax($f_0$), Emin($f_0$), Eφ($f_0$) using three graphs with rotation speed values $Aω_0$ shown on the abscissa.

According to another characteristic of the invention, the processing method includes the following steps:

for each rotation speed ω, extract one of the series Emax($f_i$), Emin($f_i$), represent the spectral decomposition of at least one of the data Emax($f_i$) or Emin($f_i$) in a cascade, thee abscissas axis corresponding to the frequency values, the ordinates axis corresponding to the magnitude of the represented data, and the axis of the dimensions corresponding to the rotation speed.

The processing in the method according to the invention may be done either off line using measurement records made as part of a previous test campaign, or in real time.

In the latter case, the method according to the invention also uses:

at least one set of two position sensors placed approximately in the same plane and with two approximately orthogonal measurement directions X and Y, at least one set of two measurement series x(t) and y(t) using two position sensors, a recording of measurement series x(t) and y(t).

Preferably, but not strictly necessarily, the method also consists of the following steps to provide information about the rotation speed ω of the rotor being studied:

install means of measuring the rotation speed ω of the rotor, make measurements of the rotation speed ω, associate the corresponding rotation speed ω with each pair of measurement series [x(t), y(t)], save the measurement series [ω[x(t),y(t)]]

The invention also relates to a device for using the processing method according to the invention.

This type of device then comprises at least:

means of reading records of x(t), y(t) measurement series, appropriate calculation means for making a spectral decomposition by DFT (Discrete Fourier Transform), of the x(t) and y(t) series and for calculating a spectral decomposition of the trajectory of the bearing block or the shaft of the rotor of the rotating machine into elementary ellipses, starting from the spectral compositions, means of recording the spectral decomposition into elementary ellipses [Emax($f_i$), Emin($f_i$), Eφ($f_i$)], and means of display and/or printout.

In the case of a device designed to perform real time processing, the device also comprises:

at least one set of two position sensors, placed approximately in the same plane and with two approximately orthogonal measurement directions X and Y, means of making and recording at least one set of two measurement series x(t) and y(t) using two position sensors.

Preferably but not strictly necessarily, the device also comprises:

means of measuring the rotation speed ω of the machine, means of associating a measurement of the rotation speed ω with, measurement series x(t) and y(t).

Various other characteristics of the invention will become clear from the following with reference to the attached drawings that illustrate one preferred but non-restrictive embodiment of how to use the method according to the invention, and how to make the device according to the invention for processing vibration measurements on a bearing block or a rotor of a rotating machine.

Figure 1:
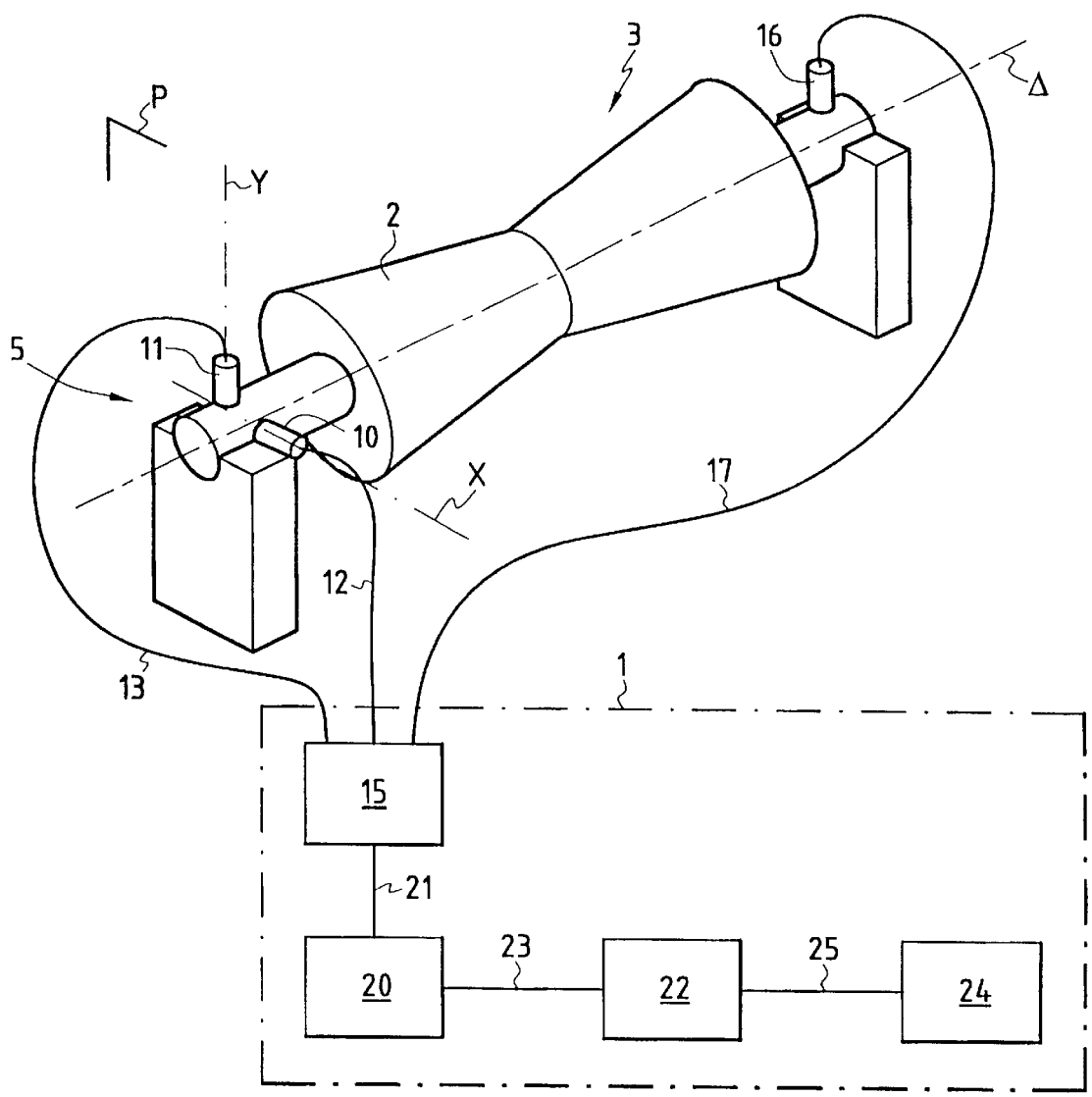
FIG. 1 is a diagrammatic view of a device for studying vibrations of a rotating machine conform with the invention.

A device according to the invention like that illustrated in FIG. 1 and denoted as a whole by reference 1, is designed to analyze vibrations of a rotor 2 of a rotating machine 3. Within the scope of the invention, the term <<rotor>> should be understood in the broad sense of the term as consisting of any element free to rotate of a rotating machine 3, for example such as but not exclusively a steam turbine, a compressor turbine, a rotor of an electric motor, of a gas turbine or of a generator.

Figure 2:
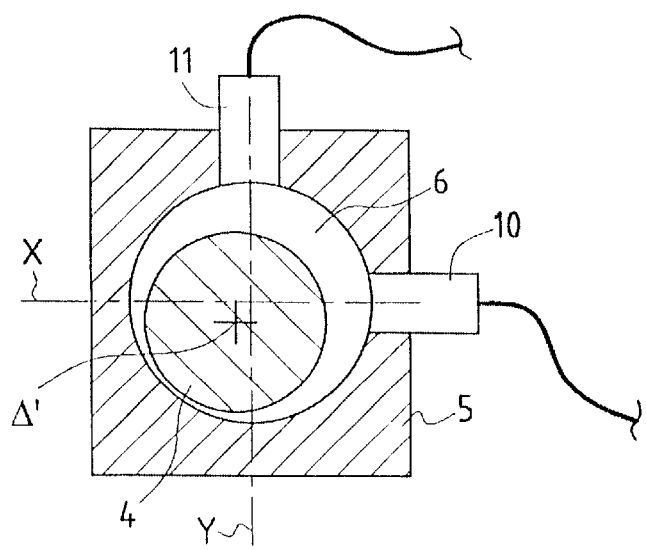
FIG. 2 is a diagrammatic view along plane P in FIG. 1 of a fluid bearing block studied using the method and the device according to the invention.

According to the illustrated example and as shown particularly in FIG. 2, the device 1 is designed to study the rotational behavior of a shaft 4 supported and guided by a bearing block with an oil film 5.

The device 1 is then particularly suitable for studying the rotational trajectory of the shaft 4 within the guide chamber 6 during operation of the rotating machine 1. Consequently, the device 1 uses two position sensors 10 and 11 placed in the same plane P approximately perpendicular to the axis of rotation Δ of the rotating machine 3. The measurement directions X and Y of the position sensors 10 and 11 are orthogonal. Thus, sensors 10 and 11 can supply the coordinates x(t) and y(t) of the Δ' axis in the plane P during rotation of shaft 5, in real time. According to the illustrated example, sensors 10 and 11 are proximity sensors. However, it would also be possible to consider using accelerometer or velocimeter type seismic sensors placed on the body of the bearing block 5.

The position sensors 10 and 11, are connected through lines 12 and 13 to respectively measurement and sampling means 15 forming an integral part of device 1.

The installation also comprises means 16 of measuring the rotation speed ω of the rotating machine 3. The measurement means 16 are also connected through a line 17 to the measurement and sampling means 15.

The device 1 also comprises means 20 of recording measurements made and sampled by means 15. The recording means 20 are also connected through a line 21 to the measurement and sampling means 15. The device 1 then also comprises calculation means 22 connected through a line 23 to the recording means 20. The calculation means 22 are then adapted to process stored information recorded in means 20. The device also comprises display means 24 such as a screen or a printer, connected through a line 25 to the calculation means 22.

It should be noted that the measurement and processing device according to the invention may for example consist of a personal computer plus data acquisition units, for example associated with analogue/digital conversion means, and operating according to a data acquisition processing program adapted to implement the process according to the invention. However, the device 1 could also consist of any dedicated unit that includes all components necessary for using the process according to the invention as described below in real time.

The device 1 then operates as follows. One or several measurement series x(t) and y(t) are carried out by the acquisition unit 15, and associated with the rotation speed ω(t) of the rotating machine. These sets of measurement series are then saved in the storage and recording means 20.

The recorded data x(t), y(t) ω(t), are then read and processed by the calculation unit 22 so that firstly a spectral decomposition is carried out on them to determine an amplitude-phase pair using a Discrete Fourier Transform calculated based on an FFT (Fast Fourier Transform) algorithm. This type of algorithm is well known to those skilled in the art and no further explanations are necessary. For example, a broader description of these algorithms can be found in the book "*Traitement numérique du signal, théorie et pratique* (*Digital signal processing, theory and practice*)—7$^{th}$ edition by M. Bellanger.

The result is a spectral decomposition of data series x(t) and y(t) in amplitude and phase [Ax(f$_i$), Φx(f$_i$)] and [Ay(f$_i$), Φy(f$_i$)]. Preferably, the spectral decompositions in amplitude-phase [Ax(f$_i$), Φx(f$_i$)] and [Ay(f$_i$), Φy(f$_i$)] are associated with the corresponding rotation speed ω.

According to the invention, the next step is to calculate a spectral decomposition into elementary elliptical trajectories of the displacement of the axis Δ' of the shaft or rotor 4 in the plane P, starting from the spectral decompositions [Ax(f$_i$), Φx(f$_i$)] and [Ay(f$_i$), Φy(f$_i$)].

Figure 3:
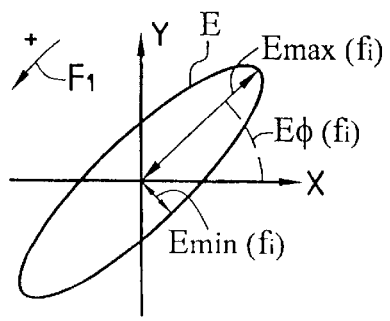
FIG. 3 is a diagrammatic view showing an elementary decomposition ellipse of the spectral decomposition of the rotation of a rotor studied using the method and device according to the invention.

For each decomposition frequency f$_i$, this spectral decomposition into elementary ellipses is defined by three data or coefficients, namely Emax(f$_i$), Emin(f$_i$), Eφ(f$_i$). As can be seen in FIG. 3, the coefficient Emax(f$_i$) corresponds to the maximum radius of the elementary ellipse at frequency f$_i$, which is the half-length of the major axis of the ellipse E. Similarly, Emin(f$_i$) is the minimum radius of the elementary ellipse at frequency fi, or half of the small-axis of the ellipse E. Finally, the coefficient Eφ(f$_i$) corresponds to the value of the angle of orientation of the main axis or the major axis of the elementary ellipse E with respect to the abscissas axis X. Eφ(f$_i$) is between 0° and 180°. The data Eφ(f$_i$) is then signed and it may be positive or negative depending on the direction of motion of the ellipse E. A positive sign denotes a movement direction along the positive clockwise direction as shown by the arrow F$_1$, and obviously a negative sign corresponds to a movement in the opposite direction.

According to one preferred embodiment of the invention, the spectral decomposition is done using a FFT (Fast Fourier Transform) algorithm using complex numbers and the calculation unit 22 is adapted to carry out operations on complex numbers. The spectral decomposition into elementary elliptical trajectories is made as follows.

The complex Fourier Transform of the x(t)+jy(t) signal gives frequency components directly, usually in the form of rectangular coordinates:

x(t)+jy(t)→R(f)+j I(f) where f can be positive (f$_i$) or negative (−f$_i$).

The spectrum can also be expressed in polar coordinates (amplitude and phase):

$$A(f)=[(R(f)^2+I(f)^2]^{1/2}$$

$$\Phi(f)=Atan(I(f)/R(f))$$

The recomposition of positive and negative frequencies gives descriptive magnitudes of each elementary ellipse:

$$Emax(f_i)=(A(f_i)+A(-f_i))/2$$

$$Emin(f_i)=Abs(A(f_i)-A(-f_i))/2$$

Movement direction $S(f_i)=Sign(A(f_i)-A(-f_i))$

Orientation of the ellipse $E\varphi_0(f)=(\Phi(f_i)+\Phi(-f_i))/2$ (modulo 180)

Hence $E\varphi(f_i)=S(f_i)E\varphi_0(f)$

It is also possible to use a real Fourier Transform giving the phased spectra [Ax(f$_i$), Φx(f$_i$)] and [Ay(f$_i$), Φy(f$_i$)] of the two sensors. Firstly, a spectral decomposition of the movement in positive frequencies and in negative frequencies is calculated as follows.

Thus, the calculations carried out in complex numbers for positive frequencies are as follows:

$x(t)$:[Ax(f$_i$), Φx(f$_i$)]→Ax(f$_i$)Cos(Φx(f$_i$))+j Ax(f$_i$)Sin(Φx(f$_i$))

$y(t)$:[Ay(f$_i$), Φy(f$_i$)]→Ay(f$_i$)Cos(Φy(f$_i$))+j Ay(f$_i$)Sin(Φy(f$_i$))

$jy(t)$:−Ay(f$_i$)Sin(Φy(f$_i$))+j Ay(f$_i$)Cos(Φy(f$_i$))

$x(t)+jy(t)$:[Ax(f$_i$)Cos(Φx(f$_i$))−Ay(f$_i$)Sin(Φy(f$_i$))]+j[Ax(f$_i$)Sin(Φx(f$_i$))+Ay(f$_i$)Cos(Φy(f$_i$))]

Giving the following decomposition in positive spectrum [A(f$_i$),Φ(f$_i$)] hence:

$$A(f_i)=[(Ax(f_i))^2+(Ay(f_i))^2+2Ax(f_i)Ay(f_i)\sin(\Phi x(f_i)-\Phi y(f_i))]^{1/2},$$

$$\Phi(f_i)=Atan[Ax(f_i)Cos(\Phi x(f_i))-Ay(f_i)Sin(\Phi y(f_i))]/[Ax(f_i)Sin(\Phi x(f_i))+Ay(f_i)Cos(\Phi y(f_i))])$$

Similarly, the calculations carried out in complex numbers for negative frequencies are as follows:

$$x(t):[Ax(-f_i), \Phi x(-f_i)] \to Ax(-f_i)Cos(\Phi x(-f_i))-j\,Ax(-f_i)Sin(\Phi x(-f_i))$$

$$y(t):[Ay(-f_i), \Phi y(-f_i)] \to Ay(-f_i)Cos(\Phi y(-f_i))-j\,Ay(-f_i)Sin(\Phi y(-f_i))$$

$$jy(t):Ay(-f_i)Sin((\Phi y(-f_i))+j\,Ay(-f_i)Cos(\Phi y(-f_i))$$

$$x(t)+jy(t):[Ax(-f_i)Cos(\Phi x(-f_i))+Ay(-f_i)Sin(\Phi y(-f_i))]+j[-Ax(-f_i)Sin(\Phi x(-f_i))+Ay(-f_i)Cos(\Phi y(-f_i))]$$

Giving the following decomposition in negative frequency spectrum $[A(-f_i),\Phi(-f_i)]$, hence:

$$A(-f_i)[(Ax(-f_i))^2+(Ay(-f_i))^2-2Ax(-f_i)Ay(-f_i)sin(\Phi x(-f_i)-\Phi y(-f_i))]^{1/2},$$

$$\Phi(-f_i)=Atan[Ax(-f_i)Cos(\Phi x(-f_i))+Ay(f_i)Sin(\Phi y(-f_i))]/[-Ax(-f_i)Sin(\Phi x(-f_i))+Ay(-f_i)Cos(\Phi y(-f_i))]$$

Finally, the coefficients of the spectral decomposition into elementary ellipses are calculated as follows:

$$Emax(f_i)=(A(f_i)+A(-f_i))/2$$

$$Emin(f_i)=Abs(A(f_i)-A(-f_i))/2$$

Direction of precession or path of the elementary ellipse $S(f_i)=Sign(A(f_i)-A(-f_i))$ Orientation of the ellipse $E\phi_0(f_i)=(\Phi(f_i)+\Phi(-f_i))/2$ (modulo 180)

Hence $E\phi(f_i)=S(f_i)\,E\phi_0(f)$

A geometric transformation needs to be applied to $E\phi_0(f_i)$ as a function of the arrangement of the X and Y sensors.

The calculated data thus give a spectral decomposition into elementary ellipses $Emax(f_i)$, $Emin(f_i)$, $E\phi(f_i)$ for the rotation speeds ω associated with the measurement series x(t) and y(t), and this spectral decomposition is recorded in the data storage means 20.

As a function of the needs of a user of the device 1, these data may be used in different ways in the form of graphic representations displayed on a screen, or printed.

Figure 4:
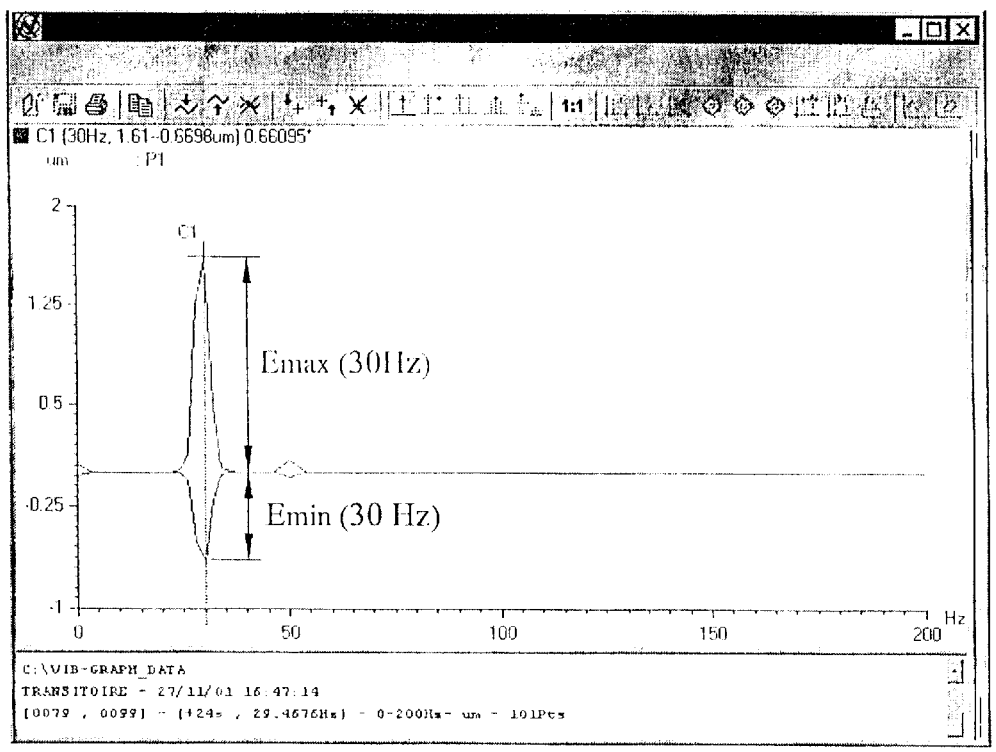
FIGS. 4 to 6 illustrate different possible forms in which results obtained using the processing method according to the invention can be represented.

According to one form of graphic representation displayed on a screen and more particularly illustrated in FIG. 4, for example all values Emax, Emin for the same rotation speed ω can be shown on a graph, with the values Emax being oriented upwards while the values Emin are oriented downwards. Thus, in FIG. 1, the values Emax and Emin for a 30 Hz frequency are signaled particularly with the indications $Emax(f_i)$, $Emin(f_i)$ and $E\phi(f_i)$ at the position of a cursor on the screen.

Figure 5:
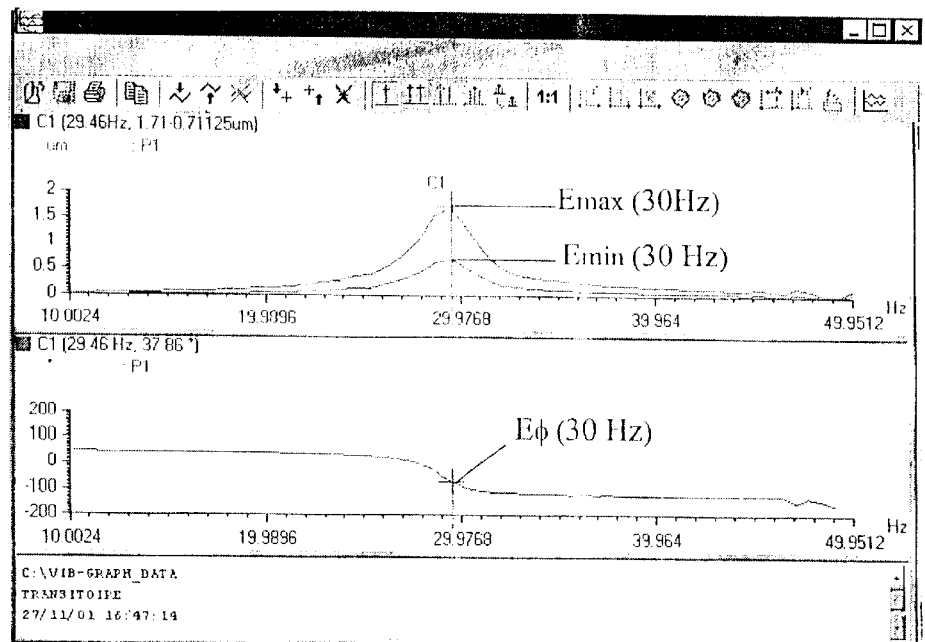

According to another analysis method according to the invention and illustrated in FIG. 5, the variation of all three data $Emax(f_i)$, $Emin(f_i)$, $E\phi(f_i)$ as a function of the rotation speed is shown on graphs, in which the abscissas axis corresponds to a multiple $A\omega_0$ of the rotation speed, while the ordinates axis corresponds to the values $Emax(f_i)$, $Emin(f_i)$, $E\phi(f_i)$, where $fi=A\omega_0$. This type of view is called a <<Bode>> view.

Figure 6:
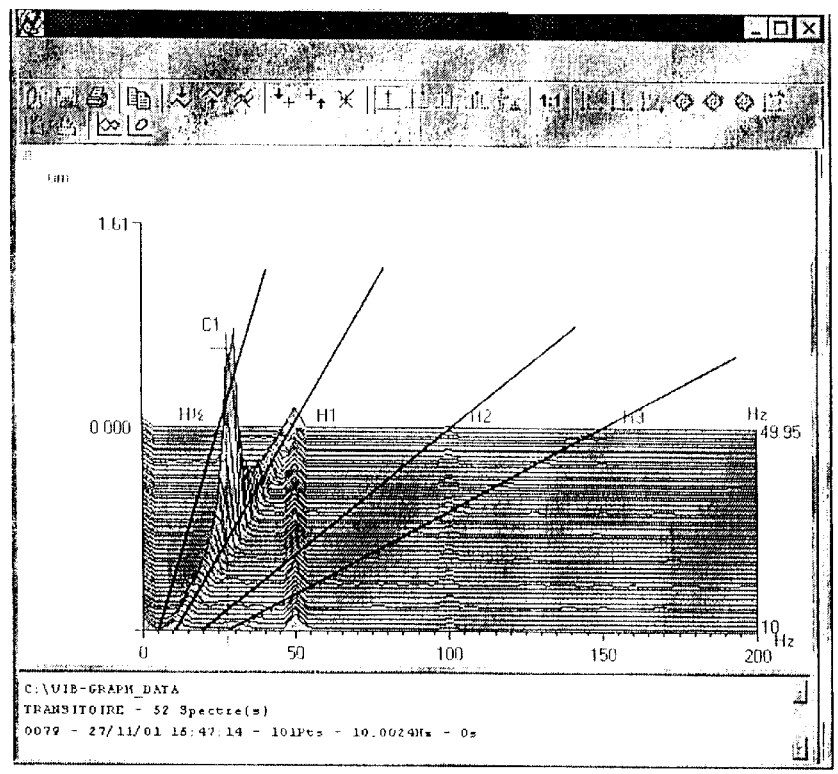

According to another analysis method, a <<cascade>> or <<three dimensional>> view is made of one of the Emax or Emin coefficients. According to the example specifically illustrated in FIG. 6, the magnitude Emax of the spectral decomposition is thus shown, the abscissas axis corresponding to the values of the decomposition frequency $f_i$, while the ordinates axis corresponds to the value of the magnitude shown, and the dimensions axis corresponds to the rotation speed ω. Note that according to the invention, the spectral decomposition is preferably made at frequencies that are multiples of the rotation frequency and FIG. 4 shows lines H1/2, H1, H2, H3 corresponding to orders, namely integer multiples or integer fractions of the rotation speed ω.

The different rotation modes of the rotor can then be identified on this type of view.

Obviously, other graphic viewing modes could be made based on the spectral decomposition of the rotation movement of a rotor into elementary ellipses, according to the invention.

Furthermore, note that spectral decomposition into elementary ellipses is a means of identifying the directions of some constraints applied to the rotor to the extent that the major axis of an elementary ellipse is perpendicular to the direction along which a constraint is applied to the rotor.

According to the example embodiment of the method described above, the calculation of the spectral decomposition into elementary ellipses is made by calculations on complex numbers. However according to the invention, this spectral decomposition can also be made by calculations on real numbers. In this case, for example, the calculation means 22 make a DFT (Discrete Fourier Transform) in sine, DFT-sin, of the x(t) and y(t) series to obtain a spectral decomposition $[Ax(f_i), \Phi x(f_i)]$ and $[Ay(f_i), \Phi y(f_i)]$ in sine. Each signal x(t) and y(t) can thus be broken down into a sum of sinusoidal signals with frequency $f_i$:

$$x(t)=\Sigma_i\,Ax(f_i)Sin(2\pi f_i\,t+\Phi x(f_i)) \text{ and } y(t)=\Sigma_i\,Ay(f_i)Sin(2\pi f_i\,t+\Phi y(f_i))$$

For a given frequency $f_i$, the combination of two sinusoidal functions describes the ellipse E. Its radius follows the following formulation:

$$R(t)^2=Ax(f_i)^2\,Sin(2\pi f_i t+\Phi x(f_i))^2+Ay(f_i)^2 Sin(2\pi f_i t+\Phi y)^2$$

$$R(t)^2=\tfrac{1}{2}(Ax(f_i)^2(1-Cos(4\pi f_i t+2\Phi x(f_i)))+Ay(f_i)^2(1-Cos(4\pi f_i t+2\Phi y(f_i))))$$

$$R(t)^2 = \frac{1}{2}(Ax(f_i)^2 + Ay(f_i)^2 - Ax(f_i)^2 Cos(4\pi f_i t + 2\Phi x(f_i)) - Ay(f_i)^2 Cos(4\pi f_i t + 2\Phi y(f_i))))$$

$$R(t)^2 = \frac{1}{2}(Ax(f_i)^2 + Ay(f_i)^2 - Ax(f_i)^2(Cos(4\pi f_i t)Cos(2\Phi x(f_i)) - Sin(4\pi f_i t)Sin(2\Phi x(f_i))) - Ay(f_i)^2(Cos(4\pi f_i t)Cos(2\Phi y(f_i)) - Sin(4\pi f_i t)Sin(2\Phi y(f_i))))$$

$$R(t)^2 = \frac{1}{2}(Ax(f_i)^2 + Ay(f_i)^2 - Cos(4\pi f_i t)(Ax(f_i)^2 Cos(2\Phi x(f_i)) +$$

-continued $$Ay(f_i)^2\mathrm{Cos}(2\Phi y(f_i))) + \mathrm{Sin}(4\pi f_i t)(Ax(f_i)^2\mathrm{Sin}(2\Phi x(f_i)) + Ay(f_i)^2\mathrm{Sin}(2\Phi y(f_i))))$$

Namely $$R(t)^2 = \tfrac{1}{2}(Ax(f_i)^2 + Ay(f_i)^2 - \mathrm{Cos}(4\pi f_i t)\, B(f_i) + \mathrm{Sin}(4\pi f_i t)\, C(f_i)) \text{ where:}$$

$$B(f_i) = (Ax(f_i)^2\mathrm{Cos}(2\Phi x(f_i)) + Ay(f_i)^2\mathrm{Cos}(2\Phi y(f_i)))$$

$$C(f_i) = (Ax(f_i)^2\mathrm{Sin}(2\Phi x(f_i)) + Ay(f_i)^2\mathrm{Sin}(2\Phi y(f_i)))$$

If we set:

$$-\mathrm{Cos}(4\pi f_i t)\, B(f_i) + \mathrm{Sin}(4\pi f_i t)\, C(f_i) = Z(f_i)\mathrm{Cos}(4\pi f_i t + \Phi z(f_i))$$

$$-\mathrm{Cos}(4\pi f_i t) B(f_i) + \mathrm{Sin}(4\pi f_i t) C(f_i) = Z(f_i)\mathrm{Cos}(4\pi f_i t)\mathrm{Cos}(\Phi z(f_i)) - Z(f_i)\mathrm{Sin}(4\pi f_i t)\mathrm{Sin}(\Phi z(f_i))$$

$$B(f_i) = -Z(f_i)\mathrm{Cos}(\Phi z(f_i))$$

$$C(f_i) = -Z(f_i)\mathrm{Sin}(\Phi z(f_i))$$

therefore:

$$\mathrm{Tan}(\Phi z(f_i)) = C(f_i)/B(f_i) \text{ hence } \Phi z(f_i) = \mathrm{Atan}\_i\, C(f_i)/B(f_i)), \text{ where } \Phi z(f_i) \text{ between } -\pi/2 \text{ and } \pi/2$$

$$Z(f_i)^2 = B(f_i)^2 + C(f_i)^2 = Ax(f_i)^4 + Ay(f_i)^4 + 2Ax(f_i)^2 Ay(f_i)^2 \mathrm{Cos}(2\Phi x(f_i) - 2\Phi y(f_i))$$

$\Phi z(f_i)$ is determined to the nearest $\pi$, and $Z(f_i)$ may be positive or negative.

If we fix $Z(f_i) > 0$ then $\Phi z = \mathrm{Atan}(C/B) + \pi(1 + \mathrm{sign}(B))/2$ i.e. we add $\pi$ if $B > 0$ since:

$$\Phi z(f_i) \text{ between } -\pi/2 \text{ and } \pi/2 \Rightarrow \mathrm{Cos} > 0$$

$$R(t)^2 = \tfrac{1}{2}(Ax(f_i)^2 + Ay(f_i)^2 + Z(f_i)\mathrm{Cos}(4\pi f_i t + \Phi z(f_i)))$$

$$Emax(f_i)^2 = \tfrac{1}{2}(Ax(f_i)^2 + Ay(f_i)^2 + Z(f_i))$$

$$Emin(f_i)^2 = \tfrac{1}{2}(Ax(f_i)^2 + Ay(f_i)^2 - Z(f_i))$$

$$Tmax: 4\pi f_i tmax + \Phi z(f_i) = 0 \Rightarrow tmax = -\Phi z(f_i)/4\pi f_i t$$

$$E\phi_0(f_i) = \mathrm{Atan}(Ay(f_i)\mathrm{Sin}(2\pi f_i tmax + \Phi y(f_i))/Ax(f_i)\mathrm{Sin}(2\pi f_i tmax + \Phi x(f_i)))$$

$$E\phi_0(f_i) = \mathrm{Atan}(Ay(f_i)\mathrm{Sin}(\Phi y(f_i) - \Phi z(f_i)/2)/Ax(f_i)\mathrm{Sin}(\Phi x(f_i) - \Phi z(f_i)/2))$$

Rotation direction calculation:

$$\text{Vector } R:(Ax(f_i)\mathrm{Sin}(2\pi f_i t + \Phi x(f_i)), Ay(f_i)\mathrm{Sin}(2\pi f t + \Phi y(f_i)), 0)$$

$$\text{Vector } dR/dt: 2\pi f(Ax(f_i)\mathrm{Cos}(2\pi f_i t + \Phi x(f_i)), Ay(f_i)\mathrm{Cos}(2\pi f_i t + \Phi y(f_i)), 0)$$

The component $Z$ of $R \wedge dR/dt = 2\pi f Ax(f_i)Ay(f_i)(\mathrm{Sin}(2\pi f_i t + \Phi x(f_i))\mathrm{Cos}(2\pi f_i t + \Phi y(f_i)) -$ $$\cos(2\pi f_i t + \Phi x(f_i))\mathrm{Sin}(2\pi f_i t + \Phi y(f_i))) = 2\pi f\, Ax(f_i)\, Ay(f_i)\, (\mathrm{Sin}(\Phi x(f_i) - \Phi y(f_i)))$$

The direction of movement is: $S(f_i) = \mathrm{sign}(Ax(f_i)\, Ay(f_i)\mathrm{Sin}(\Phi y(f_i) - \Phi y(f_i)))$ $$E\phi_0(f_i) = E\phi_0(f_i)\, S(f_i)$$

Obviously, the spectral decomposition into elementary ellipses conform with the invention could also be made using Discrete Fourier Transforms in cosine.

What is claimed is:

1. Method for processing measurements of the vibration of a bearing block (5) or a rotor (2) of a rotating machine (3) comprising:

using a record of at least one pair of two series of measurements x(t) and y(t) made using at least one pair of two position sensors (10, 11) placed relative to the bearing block (5) or the rotor (2) and arranged approximately in the same plane (P) and with two approximately orthogonal measurement directions X and Y, calculating a DFT (Discrete Fourier Transform) of each of the two series x(t) and y(t) to obtain a spectral decomposition of the series x(t) and y(t) in amplitude and phase according to two series of amplitude-phase pairs $[Ax(f_i), \Phi x(f_i)]$ and $[Ay(f_i), \Phi y(f_i)]$ where $f_i$ corresponds to frequency values distributed on the frequency spectrum, characterized in that it also comprises:

starting from spectral decompositions $[Ax(f_i), \Phi x(f_i)]$ and $[Ay(f_i), \Phi y(f_i)]$, calculating a spectral decomposition in elementary elliptical trajectories of the displacement of the rotor axis, defined by a series of sets of at least three data $[Emax(f_i), Emin(f_i), E\phi(f_i)]$ where:

$Emax(f_i)$ is the maximum radius of the elementary ellipse at frequency $f_i$, $Emin(f_i)$ is the minimum radius of the elementary ellipse at frequency $f_i$, $E\phi(f_i)$ corresponds to the value of the orientation angle of the principal axis of the elementary ellipse, and may be positive or negative depending on the direction of movement around the ellipse, Save the series $[Emax(f_i), Emin(f_i), E\phi(f_i)]$.

2. Processing method according to claim 1, comprising:

using a FFT (Fast Fourier Transform) algorithm using complex numbers, making a spectral decomposition of the rotation movement, firstly for positive frequencies and secondly for negative frequencies, giving two series $[A(f_i), \Phi(f_i)]$ and $[A(f_i), \Phi(-f_i)]$, starting from positive frequency spectra and negative frequency spectra, calculating the spectral decomposition into elementary ellipses using the following formulas:

$$Emax(f_i) = [A(f_i) + A(f_i)]/2$$

$$Emin(f_i) = \mathrm{Abs}[(A(f_i) - A(-f_i)]/2]$$

$$S(f_i) = \mathrm{Sign}[A(f_i) - A(-f_i)]$$

$$E\phi_o(f_i) = [\Phi(f_i) - \Phi(-f_i)]/2$$

$$E\phi(f_i) = S(f_i) \times E\phi_o(f_i).$$

3. Processing method according to claim 1, comprising:

making a DET-sin (Discrete Fourier Transform in sine) of the x(t) and y(t) series to obtain a spectral decomposition $[Ax(f_i), \Phi x(f_1)]$ and $[Ay(f_i), \Phi y(f_i)]$ in sine, using the sine spectral compositions to make a spectral decomposition into elementary ellipses $[Emax(f_i), Emin(f_i), E\phi(f_i)]$.

4. Processing method according to claim 1, comprising:

making a record of several pairs of series of measurements x(t) and y(t), each pair [x(t), y(t)] being associated with a rotation speed ω(t) of the rotor, associating the corresponding rotation speed ω with the spectral decomposition of each pair x(t), y(t), into amplitude-phase [Ax($f_i$), Φx($f_i$)] and [Ay($f_i$), Φx($f_i$)], and associating the rotation speed ω with the spectral decomposition into elementary elliptical trajectories [Emax($f_i$), Emin($f_i$), Eφ($f_i$)], recording the set [ω[Emax($f_i$), Emin($f_i$), Eφ($f_i$)].

5. Processing method according to claim 4, comprising:

selecting a rotation speed ω extracting the spectral decomposition into elementary ellipses [Emax($f_i$), Emin($f_i$), Eφ($f_i$)] associated with ω and representing the spectral decomposition into elementary ellipses [Emax($f_i$), Emin($f_i$), Eφ($f_i$)], for this value of the rotation speed, using three graphs in an orthogonal coordinate system in which the abscissa axes correspond to the frequencies.

6. Processing method according to claim 4, comprising:

selecting a given frequency $f_n$=Aω in the decomposition spectrum, for this frequency $f_n$ and for each rotation speed, extracting the values Emax($f_n$), Emin($f_n$), Eφ($f_n$), and making a graphic <<Bode>> representation of the coefficients Emax($f_n$), Emin($f_n$), Eφ($f_n$) using three graphs with rotation speed values shown on the abscissa.

7. Processing method according to claim 4, comprising:

for each rotation speed, extracting one of the series Emax($f_i$), Emin($f_i$), representing the spectral decomposition of at least one of the data Emax($f_i$) or Emin($f_i$), in a cascade, the abscissas axis corresponding to the frequency values, the ordinates axis corresponding to the magnitude of the represented data, and the axis of the dimensions corresponding to the rotation speed.

8. Processing method according to claim 1, comprising:

using at least one set of two position sensors (10, 11), placed approximately in the same plane (P) and with two approximately orthogonal measurement directions X and Y, making at least one set of two measurement series x(t) and y(t) using two position sensors (10,11), recording measurement series x(t) and y(t).

9. Processing method according to claim 8, comprising:

installing means (16) of measuring the rotation speed of the rotor (2), making measurements of the rotation speed ω, associating the corresponding rotation speed ω with each pair of measurement series [x(t), y(t)], recording the measurement series [ω[x(t),y(t)]].

10. Device for using the processing method according to claim 1, comprising:

means (20) of reading records of x(t), y(t) measurement series, appropriate calculation means (22) for making a spectral decomposition by DFT (Discrete Fourier Transform), of the x(t) and y(t) series and for calculating a spectral decomposition into elementary ellipses of the trajectory of the axis Δ' of the rotor (2) of the rotating machine (3), starting from the spectral compositions, means of recording the spectral decomposition into elementary ellipses [Emax($f_i$), Emin($f_i$), Eφ($f_i$)], means of display and/or printout.

11. Device according to claim 10, comprising:

at least one set of two position sensors (10, 11), placed approximately in the same plane (P) and with two approximately orthogonal measurement directions X and Y, means (15) of making and recording at least one set of two measurement series x(t) and y(t) using two position sensors (10, 11).

12. Device according to claim 10, comprising:

means (16) of measuring the rotation speed of the machine, means (15) of associating a measurement of the rotation speed with measurement series x(t) and y(t).

\* \* \* \* \*